(12) United States Patent
De Gregorio

(10) Patent No.: US 8,114,861 B2
(45) Date of Patent: Feb. 14, 2012

(54) COMPOSITIONS CONTAINING COMPOUNDS HAVING STEROID STRUCTURE AND THEIR USE FOR INDUCING THE PROLIFERATION AND DIFFERENTIATION OF STEM CELLS OF THE ORGANISM

(75) Inventor: Chiara De Gregorio, Cori (IT)

(73) Assignee: Codex V S.R.L., Cori (IT)

( * ) Notice: Subject to any disclaimer, the term of this patent is extended or adjusted under 35 U.S.C. 154(b) by 69 days.

(21) Appl. No.: 12/532,000

(22) PCT Filed: Mar. 19, 2008

(86) PCT No.: PCT/IB2008/000651
§ 371 (c)(1),
(2), (4) Date: Oct. 15, 2009

(87) PCT Pub. No.: WO2008/114125
PCT Pub. Date: Sep. 25, 2008

(65) Prior Publication Data
US 2010/0113403 A1 May 6, 2010

(30) Foreign Application Priority Data
Mar. 21, 2007 (IT) .............................. MI2007A0561

(51) Int. Cl.
*A61K 31/56* (2006.01)
(52) U.S. Cl. ..................................................... 514/170
(58) Field of Classification Search .................. None
See application file for complete search history.

(56) References Cited

U.S. PATENT DOCUMENTS
5,252,331 A * 10/1993 Curtis et al. .................. 424/401
2003/0021850 A1 1/2003 Xu
2006/0198898 A1 9/2006 Xu FOREIGN PATENT DOCUMENTS
WO WO 02/067876 * 9/2002
WO WO 02/067876 A1 9/2002
WO WO 03/001982 A2 1/2003

OTHER PUBLICATIONS

International Olive Oil Council (Determination of the Composition and Content of Sterols by Capillary-Column Gas Chromatography, published 2001).*

* cited by examiner

*Primary Examiner* — Brandon Fetterolf
*Assistant Examiner* — Craig Ricci
(74) *Attorney, Agent, or Firm* — Arent Fox LLP

(57) ABSTRACT

Use of a mixture of phytosterols, selected from the group comprising: brassicasterol (Delta 5-C22 unsaturated); campesterol; campestanol; stigmasterol (Delta 5-C22 unsaturated); Delta 5-C23-stigmastadienol; clerosterol (Delta 8-C25 unsaturated); Beta-sitosterol; sitostanol; Delta 5-venasterol (Delta 5-C24 unsaturated); Delta 5-C24-stigmastadienol (Delta 5-C24 diene unsaturated); Delta 7-stigmastenol; 24-methylene-cycloartenol; gramisterol; 24-methylcholest-7-enol; isofucosterol; Delta 7-avenasterol (Delta 7-C24 unsaturated); Delta 5-avenastenol, for the manufacture of a medicament to induce into the adult organism proliferation and differentiation of the stem cells which are present in the organism.

7 Claims, No Drawings

COMPOSITIONS CONTAINING COMPOUNDS HAVING STEROID STRUCTURE AND THEIR USE FOR INDUCING THE PROLIFERATION AND DIFFERENTIATION OF STEM CELLS OF THE ORGANISM

CROSS-REFERENCED TO RELATED APPLICATION

This application is a National Stage entry of International Application No. PCT/IB2008/000651, filed Mar. 19, 2008, which claims priority to Italian Patent Application MI2007A000561, filed Mar. 21, 2007, the disclosure of the prior application is incorporated in its entirety by reference.

The present invention relates to the use of phytosterols, preferably in combination with 24-methylene-cholesterol and/or cholesterol, for the manufacture of a medicament to induce in an adult organism proliferation and differentiation of the stem cells which are present in said organism, for obtaining regeneration, through the corresponding complete substitution, of vessels and/or tissues diseased and/or damaged by different types of pathologies and/or by ageing.

The present invention also relates to the use of said substances for the manufacture of a medicament to induce proliferation and differentiation of the stem cells in an adult organism for restoring, by rebalancing it, the organism systemic immune response at peripheral and/or central level, to the attack of pathogens of different nature and origin, to cellular necrosis, to the formation of neoplastic cells.

In a completely unexpected way, said medicament proved useful for inducing in the adult organism proliferation and differentiation of the stem cells, which are present in the different districts/tissues of the body in a quiescent state, in accordance with the need of the district/tissue of interest and also beyond the possible physiological capabilities of the organism.

Said medicament is suitable for transdermal and/or transmucosal administration.

STATE OF THE ART

It is known in the art that stem cells are constituted by an heterogeneous group of undifferentiated cells, which share the potential capability of changing into specialized, i.e., differentiated, cells which will become part of a specific tissue.

Thus stem cells form, at least theoretically, a possible supply of new cells for substituting those cells of the various human and animal tissues which are diseased, damaged, died or even only aged.

This undoubtedly applies to the embryonic stem cells, which are multipotent and active progenitor cells; namely, they are actually able to efficiently differentiate to yield all the other types of cells that the organism needs.

On the contrary, at least until recently, adult stem cells were believed to be less powerful, being less versatile: their differentiation ability seemed limited only to certain specific tissues.

Recently, it has been confirmed that multipotent stem cells also exist in the adult organism; thus, these cells should/could have the same differentiation potential as the embryonic stem cells.

It is known that stem cells remain in a quiescent state (G0) until reached by suitable signals from other cells, or blood, or other tissues, which induce their proliferation and differentiation. At this point, the proliferation cycle begins which simultaneously involves the differentiation of stem cells to give new specific cells, which will replace the corresponding damaged or diseased ones, and the restoration of the stem cells which have undergone differentiation. Stem cells are in fact characterized in a new stem cell is reproduced to replace every single stem cell that has undergone differentiation. This way, the total number of stem cells for every tissue does not change.

The above described mechanism is always active in embryonic stem cells, so that any embryo damage, as long as it is not of genetic origin, can be repaired through the activation of the embryonic stem cells which differentiate and replace the damaged part of the tissue, completely regenerating it.

Unfortunately, this does not happen in the adult organism, where the only cells always in cycle, i.e. expressing a continuous mitotic activity, are the so called transient cells. In a tissue, in which basic parenchyma consists of transient cells, the death of a high number of dead cells is rapidly replaced by the proliferation of the remaining cells until complete restoration. Examples of transient cells are represented by the cells of the epithelium, of the mucous membranes, of the hemopoietic and lymphopoietic tissues.

On the other hand, the so called stable cells have low proliferation activity: only a comparatively small fraction of the cell population is in cycle, while the major part of it is the G0 quiescent state (also including the stem cells present in the corresponding tissue). Examples of stable cells are represented by cells of liver, kidneys and pancreas parenchyma, mesenchymal cells (e.g. fibroblasts), smooth muscle cells, osteoblasts, endothelial cells.

Finally, the so called permanent cells have lost their reproductive ability. Examples of said cells are represented by neurons, the skeleton and hearth striated muscle cells and the cells of the crystalline.

This confirms that vasal and/or tissutal damages restoration (due to both endogenous or exogenous causes) through induction/activation of stem cells to differentiate and, consequently, produce novel healthy vessels and/or tissues that replace the diseased ones, is far less efficient in the adult organism compared with what happens in the embryo with the embryonic stem cells. In particular, said activation is not possible in the case of permanent cells, e.g. in the neurons, in which, in case of neuronal death, the adult organism is not able to "wake up" the existing stem cells back from their quiescence status.

Summarizing, the function of stem cells in the adult organism is to undergo differentiation into somatic cells for a specific tissue, only to replace dead cells (e.g. in the epithelium).

Unfortunately, when the cells that form a tissue undergo degeneration, ageing, or are in an atrophic or dysfunctional condition, due to pathologic problems, both endogenous or exogenous, of various origin and nature, but do not die, then there is no physiological replacement, through the entry into the cycle and the differentiation of the existing stem cells.

In other words, when a senile or degenerative pathology, of any type and origin, begins in the adult organism, since the cells affected by said pathology do not die but survive in conditions of even poorer functional efficiency, then the restoration mechanism for said damaged cells, through induction to proliferation and differentiation of the stem cells existing in the interested district, is not activated or possibly only partially activated to a degree insufficient to the need of the district. That induces the lasting of the disease. Moreover, when an infectious or oncologic pathology appears in an organism, this is due to the functional impairment/deficit condition of the immune cells of the organism district (e.g., skin and mucosae).

For example, at the skin level, the Langerhans cells are no more able to recognize the antigenic substance, to capture the antigen and to transport it to the lymph nodes, thus activating the immune response.

The inertia of this type of cells, as well as of other immune cells, causes the infectious pathology or the tumor to take place. The inertia of this type of cells means that no correct activation occurred at the lymph nodal level with the subsequent differentiation and proliferation of the lymphocyte precursor PTh→PTh0. Therefore no correct differentiation took place in the effector sub-types Th1/Th2, which are know to be at the basis of an efficient immune response involving the cell-mediated and antibody aspect.

Said insufficient differentiation is in turn due to the fact that proliferation and differentiation of lymphocyte cell stem precursor did not take place efficiently, in accordance with the need of the district.

Thus, it would be very useful to provide a medicament for inducing, when necessary, proliferation and differentiation of grown stem cells in the adult organism where they are present in a quiescent state, according to the need of the interested district, in order to obtain the regeneration, and the corresponding complete replacement, of vessels and/or tissues diseased and/or damaged by different pathologies (comprising the immune ones) and/or by ageing.

Attempts carried out by transplanting embryonic stem cells into the interested district gave promising preliminary results; nevertheless, apart from the known ethical problems involved in the use of embryonic stem cells, any rejection reactions by the organism to the introduction of foreign material cannot be excluded.

Thus the need for a medicament such as the one above described still remains long felt by the medical class.

It is one aim of the present invention to appropriately address to the above mentioned need.

It has now unexpectedly been found that specific pharmaceutical compositions, administrable by the transdermal and/or transmucosal route, comprising a suitable mixture of phytosterols, preferably in combination with 24-methylene-cholesterol and, possibly, cholesterol, are able to match to the above disclosed technical problem.

The phytosterols have already been widely studied and suggested as drugs useful in different fields, but never for the scope of the present invention.

For example, WO 00/69404 discloses a method of regulating keratinous tissue by topical application of phytosterols, mainly for cosmetic purposes.

WO 93/21925 describes pharmaceutical compositions containing cycloartenol and derivatives with cytotoxic and anti-tumoral activity suitable for oral administration.

U.S. Pat. No. 6,555,118 discloses compositions containing extracts of various plants of Chinese origin together with an extract containing 3-sitosterol, in particular soy extract. Said compositions are indicated as useful for the treatment of wounds, burns, bedsores, diabetic ulcers, dermatitis and other inflammatory skin conditions.

EP 1046396 discloses compositions comprising soy proteins and phytosterols useful for the reduction of LDL cholesterol.

WO 00/72862 discloses a cranberry seed oil comprising fatty acids as main components and tocochromanols, flavonoids, terpenes and phytosterols as minor components. Data of anti-proliferative activity against breast tumors cells are reported in particular for tocotrienols possibly in combination with flavonoids. Phytosterols are a minor part of cranberry seed oil and it is not therefore possible to draw any conclusions on the contribution that the phytosterols give to the activity described for the oil.

WO 01/03712 discloses compositions containing *Butyrospermum parkii* extract, whose main components are triterpenes (up to 33% of the extract) and possibly much lower amounts (2.2 to 2.7%) of phytosterols. Such extracts are described as useful for the treatment of chronic inflammatory or autoimmune diseases such as psoriasis, dermatitis, eczema, Crohn's disease, rheumatoid arthritis. The triterpenes are stated to be absolutely critical and essential to the observed activities, contrary to the phytosterol fraction.

US 2002/0132019 discloses sterol fractions from *Nigella sativa* useful for the treatment of bacterial and fungi infections and as anti-allergic/anti-asthma agents.

Kasahara et al. in Phytotherapy Research, Vol. 8, 1994, 327-331, disclose the antitumor effect of stigmasterol and of the *Carthami flos* extract containing it in a two stage carcinogenesis test in the mouse.

Bi Yanlan et al. in J. Agricultural and Food Chemistry, Vol. 54, 2006, 7672-7677, disclose the composition of *Lotus plumule* oil containing 14 to 19% of an insaponifiable phytosterols fraction. *Lotus plumule* oil can be utilized as a dietetic supplement for reducing cholesterol.

DESCRIPTION OF THE INVENTION

The present invention relates to the use of a mixture of phytosterols, preferably in combination with 24-methylene-cholesterol, more preferably in further combination with cholesterol, for the preparation of a pharmaceutical composition for inducing proliferation and differentiation of the stem cells in the adult organism, according to the requirement of the interested district, for obtaining the complete regeneration of vessels and/or tissues diseased and/or damaged by different types of pathologies an/or by ageing.

Another object of the present invention is the use of the above mixture for the preparation of a pharmaceutical composition for inducing proliferation and differentiation of the stem cells in the adult organism, according to the requirements of the interested district, for restoring, by rebalancing it, the organism systemic immune response, at peripheral and/or central level, to the attack of pathogens of different nature and origin, to cellular necrosis, to the formation of neoplastic cells.

It is a further object of the present invention a pharmaceutical composition comprising the above mixture.

The above mixture of the phytosterols according to the invention unexpectedly proved able to induce in the adult organism, at district level, the activation to differentiation of the stem cells present in the district, in accordance with the physiological need of the tissue, system/systems districtually involved with the lesion and/or pathology object of the intervention, with the possible central consequences at level and in favour of said systems (for example the immune system), always according to their physiological need, if dysfunctional and, accordingly, physiologically non-able to give an adequate response (which is the cause of the lesions and/or pathologies). Said possible central effects are due to the triggering of the mechanism of the cascade release of the net of suitable mediators (molecules, cytokines and growth factors) connected with, induced, related to or consequent to/provoked by the differentiation of the stem cells and to their substitution of the diseased or dysfunctional cells (for example, the Langerhans cells), with the complete restoring of their original functionality.

In a completely unexpected way, the compositions of the present invention proved able to induce proliferation and differentiation of the quiescent stem cells in a specific district of the adult organism not only in accordance with the need of said district (related to the kind, progress and severity of the pathology), but also beyond the possible physiological capability of the organism (for example, in the case of stable and permanent cells). In other words, the compositions of the present invention proved able to wake up back the adult stem cells inducing them to work (i.e., to proliferate and differentiate) in the same way as the embryonic stem cells.

This, even more unexpectedly, means that said proliferation and differentiation of the adult stem cells in the district of interest, induced by the compositions of the present invention, takes place so that the diseased vessel and/or tissue is completely regenerated (i.e., restored to the original pre-disease condition), whichever the pathology that has caused the alteration/damage. Actually, the diseased vessel and/or tissue is reabsorbed by the matrix and a new, perfectly integer, vessel and/or tissue is formed to replace it. As a consequence, the new vessel and/or tissue is not affected by the previous pathology, whichever it is (degenerative, immune, tumoral included).

As a result of the induction of proliferation and differentiation of the quiescent stem cells of the adult organism, the compositions of the present invention proved useful for the restoring treatment of disorders of the vascular system, degenerative tissue diseases, including those caused by metabolic disorders, disorders of the nervous system, of the immune system, generalised infections resistant to all treatments, advanced-stage or terminal tumours. Namely, thanks to the above differentiation of the stem cells activated by the composition of the invention, the diseased tissue is removed together with the cause itself of the disease.

As a consequence, not only the symptoms of the disease are treated, as it often happens; actually, the new vessel and/or tissue prove completely devoid of residual marks, like, scars, skin thickenings, permanent colours or decolorizations.

As above mentioned, the compositions according to the present invention comprise the following phytosterols: 24-methylene-cycloartenol, gramisterol, 24-methylcholest-7-enol, isofucosterol, stigmasterol (Delta 5-C22 unsaturated), Delta-5-avenasterol (Delta 5-C24 unsaturated), Delta-7-avenasterol (Delta 7-C24 unsaturated), brassicasterol (Delta 5-C22 unsaturated), Delta 5-C24-stigmastadienol (Delta 5-C24 diene unsaturated), clerosterol (Delta 8-C25 unsaturated), Delta-7-stigmastenol cholesterol, Beta-sitosterol, Delta-5-avenastenol, Delta 5-C23-stigmastadienol, campestanol, sitostanol, campesterol.

Among these, the ones mentioned in the following Examples 1-4 are preferred.

Particularly preferred is a mixture of phytosterols comprising: brassicasterol (Delta 5-C22 unsaturated); campesterol; campestanol; stigmasterol (Delta 5-C22 unsaturated); Delta 5-C23-stigmastadienol; clerosterol (Delta 8-C25 unsaturated); Beta-sitosterol; sitostanol; Delta-venasterol (Delta 5-C24 unsaturated); Delta 5-C24-stigmastadienol (Delta 5-C24 diene unsaturated); Delta-7-stigmastenol.

The mutual weight ratios of the phytosterols present in the active principles mixture can vary, depending on the type of formulation and pathology that the stem cells have to treat.

Preferably, the pharmaceutical compositions according to the invention can further comprise an effective amount of 24-methylene-cholesterol.

Possibly, as an alternative to 24-methylene-cholesterol, derivatives thereof having a polyene or diene chain at C-24 can be used.

In a particularly preferred embodiment, the pharmaceutical compositions of the invention comprise an effective amount of 24-methylene-cholesterol and an effective amount of cholesterol.

The phytosterols mainly derive from unsaponifiable fractions of lipid phytoextracts or vegetable oils, particularly olive, soy or wheat germ oils.

The compositions of the invention can also contain suitable amounts of beta-carotenoids and/or tocopherols and/or other vitamins.

The compositions described above will be administered by the topical, transdermal, transmucosal route, depending on the site affected by the disorder to be treated, at doses which can vary within wide limits in view of the substantial absence of toxicity of the compositions.

Broadly speaking, for the topic transdermal and/or transmucosal administration, the total weight of the active ingredients in the formulations, as a percentage of the total weight of the composition, can range between 0.001% and 25%; preferably, from 0.01% to 20%; more preferably, from 0.1% to 15%.

In a particularly preferred embodiment, the concentration of the active ingredients mixture is comprised from about 5% to about 11%.

In a further particularly preferred embodiment, said concentration is comprised from 8% to 10%.

The compositions will be prepared by using conventional methods and apparatuses, usually employed in the formulative sector.

The compositions will be suitably formulated in combination with conventional excipients or carriers and in reciprocal ratios which are well known and used by the skilled technician, optionally together with other active ingredients having a complementary or otherwise useful activity. In particular, the transdermal formulations may contain suitable well known absorption promoters in conventional use.

The phytosterols can be used in the pure form, or as a lipid extract or vegetable oil containing them. Said compounds are commercially available or can be obtained by synthesis or extraction with conventional methods. 24-ethylene-cholesterol is present in various well known vegetable extracts from which it can be isolated, or it can be used in the form of an extract.

Preferred pharmaceutical compositions of the invention comprise a mixture of active principles consisting of:
cholesterol;
brassicasterol (Delta 5-C22 unsaturated);
24-methylene-cholesterol;
campesterol;
campestanol;
stigmasterol (Delta 5-C22 unsaturated);
Delta 5-C23-stigmastadienol;
clerosterol (Delta 8-C25 unsaturated);
Beta-sitosterol;
sitostanol;
Delta 5-avenasterol (Delta 5-C24 unsaturated);
Delta 5-C24-stigmastadienol (Delta 5-C24 diene unsaturated);
Delta-7-stigmastenol.

Preferred topical (transdermal and/or transmucosal) pharmaceutical compositions of the invention comprise 10% by weight (on the total weight of the composition) of a mixture of active principles consisting of:
cholesterol;
brassicasterol (Delta 5-C22 unsaturated);
24-methylene-cholesterol;
campesterol;

campestanol;
stigmasterol (Delta 5-C22 unsaturated);
Delta 5-C23-stigmastadienol;
clerosterol (Delta 8-C25 unsaturated);
Beta-sitosterol;
sitostanol;
Delta 5-avenasterol (Delta 5-C24 unsaturated);
Delta 5-C24-stigmastadienol (Delta 5-C24 diene unsaturated);
Delta-7-stigmastenol.

The residual percent amount up to 100% is formed by a suitable mixture of excipients, carriers, absorption promoters, which are conventionally used in the field and formulated in reciprocal ratios to provide an oleogel having high dermal penetrability.

Also preferred are topical (transdermal and/or transmucosal) pharmaceutical compositions comprising 8% by weight (on the total weight of the composition) of the above disclosed mixture of active principles.

In this case, the residual percent amount up to 100% is formed by a suitable mixture of excipients, carriers, absorption promoters, which are conventionally used and formulated in reciprocal ratios such as to provide a paste having high dermal penetrability.

In a particularly preferred embodiment of the invention, the above disclosed mixture of active principles has the following composition:

| | |
|---|---|
| cholesterol; | 0.5% |
| brassicasterol (Delta 5-C22 unsaturated); | 3.6% |
| 24-methylene-cholesterol; | 0.3% |
| campesterol; | 24.9% |
| campestanol; | 1.1% |
| stigmasterol (Delta 5-C22 unsaturated); | 22.7% |
| Delta 5-C23-stigmastadienol; | 0.5% |
| clerosterol (Delta 8-C25 unsaturated); | 0.4% |
| Beta-sitosterol; | 43.1% |
| sitostanol; | 1.7% |
| Delta 5-avenasterol (Delta 5-C24 unsaturated); | 0.5% |
| Delta 5-C24-stigmastadienol (Delta 5-C24 diene unsaturated); | 0.3% |
| Delta-7-stigmastenol | 0.4% |

Preferably, the composition wherein the mixture of the above active principles is present in a percent amount corresponding to 8% by weight, on the total amount of the composition, also comprises a percent amount of zinc oxide (well known for its soothing/anti-inflammatory action) of about 10% by weight, on the total amount of the composition.

The pharmaceutical compositions of the present invention proved useful for activating/inducing the production and differentiation of the stem cells in the adult organism, in accordance with the need of the district/tissue of interest and beyond the possible physiological capabilities of the organism, for the treatment of diseases in which the regeneration of diseased vessels and/or tissues and the restoration/rebalance of the immune response of the organism is required.

Examples of pathologies included in the above definition comprise: atherosclerosis (peripheral arteriopathies and diabetic micro- and macroangiopathies), vascular lesions caused by chronic venous insufficiency and the sequelae of CVI, varicose veins, varicophlebitis or superficial or deep vein thrombosis, lymphoedema, vasculitis, dermatocellulitis, purpura (with normal blood coagulation parameters), Favre's ochre dermatitis, vasospastic disorders, rosacea, Raynaud's disease, acrocyanosis, herniosis.

The resolution of said vascular disorders has led to complete healing of chronic wounds, otherwise non-healable, with the complete "restitutio in integrum" of the diseased tissues, without formation of scars, especially in patients suffering from venous, arterial, inflammatory, lymphoedematous, diabetic and vasculitic ulcers, ischaemic or hypertensive ulcers, also including debilitated, immunocompromised, oncological and senile patients.

Examples of tissue pathologies that respond to the treatment according to the invention, among the degenerative ones caused by metabolic disorders, are diabetic skin lesions.

Examples of disorders of the immune system that respond to the treatment according to the invention include autoimmune diseases such as connective tissue disease, vasculitis, scleroderma, lupus, dermatomyositis, pemphigus and chronic inflammatory disorders, including those related with alteration of the CD4/CD8 ratio at regional level or in the peripheral blood, and chronic inflammatory disorders, degenerative arthritis, inflammatory arthritis (evaluated in the limbs), Suddek's syndrome, tendinitis, myositis and chronic inflammatory cutaneous and subcutaneous diseases such as psoriasis, allergic dermatitis, atopic dermatitis, lichen sclerosus simplex, septal and globular panniculitis.

Examples of infectious diseases that respond to the treatment include: infections of the skin and mucous membranes and subcutaneous infections tending to become chronic or with frequent flare-ups, supported by infectious agents including those resistant to conventional treatments (bacteria, fungi, dermatophytic yeasts, mixed flora, viruses, and in particular staphylococci, streptococci, Gram-negative coryneforms, mycobacteria, dermatophytes, yeasts, herpes virus, papillomavirus, poxvirus, etc.); intertrigo, acne, epididymitis, orchitis, vulvovaginitis, proctitis, balanoposthitis with sclerotic or scleroatrophic reparatory events such as phimosis, paraphimosis and synechia, generalised systemic infections, with or without rash, whether or not accompanied by manifestations of septic central inflammatory response, infections localised in tissues and/or blood vessels (venous/lymphatic disorders with consequent phlebitis, lymphangitis, adenitis and the like or selectively affecting organs or limbs) in situations that did not respond to earlier treatments.

Examples of tumours that respond to the treatment according to the invention include angiomas, benign tumours, histiocytosis, neurofibromatosis and full-blown oncological diseases such as tumours in situ (epithelioma and basal-cell carcinoma), Paget's disease and Bowen's disease affecting the limbs and lymph node stations or at an advanced stage (NH lymphomas, sarcomas, and breast tumours).

Examples of lesions of the nervous system which have responded to the treatment according to the invention include skin grafts with no sensitivity which, after being implanted to replace traumatically removed fingertips, have recovered their sensitivity; the insensitive fingers of patients who had lost sensitivity due to scleroderma have also been treated with the same result.

In particular, patients who did not respond to other known treatments or were vulnerable (diabetics, oncological patients, cachectic or immunocompromised patients and patients in circumstances that rule out systemic treatments, such as breastfeeding women with viral infections) have been successfully treated.

Some specific disorders which have responded well to the transdermal treatment with one of the gel/oleo gel or paste formulations described above and in the following Examples 3 and 4 are listed below by way of example:
erysipelas;
diabetic gangrene of the lower limbs;
decubitus gangrene in terminal or cachectic patients;
sepsis following radical surgery;

herpes zoster and other herpes infections;
porokeratosis of Mibelli;
lymphomas, especially non-Hodgkin's lymphomas;
breast cancers;
basal-cell and squamous-cell carcinomas.

On average, the treatment of said disorders required from 4-5 days to some months' application of the transdermal and/or transmucosal system (gel, oleo gel, cream, soothing paste) according to the invention.

One particularly meaningful example of successful application of the formulations according to the invention is given by the following case.

A woman, aged 97 years, was affected by erysipela. The patient was also diabetic, with a glycemia value of 300, and moreover had a diabetic ulcer which was deep to the bone and necrotic. The marks of the infection were such that also the abdominal region was involved, being dark and with clear symptoms of a current generalized sepsis. Injective anti-biotic therapy gave no positive results at all. Her relatives refused to let the woman be admitted into hospital. The topical application, twice a day, of the paste composition of Example 4, from abdomen downwards, provoked the resolution of the situation in twenty days treatment. Even the diabetic ulcer closed. The condition of the skin changed completely: the same, at the end of the treatment was elastic and the recovery of the trophism was complete.

The other following results that confirm the utility of the present invention, have been selected from a high number of positive cases.

Good results were obtained, by way of example, in a male patient, aged 57, suffering from diabetes mellitus and having, at the beginning of the therapy, a wide venous ulcer on the malleolus of the left leg. After application, twice a day, of the paste composition of Example 4, for a period of thirty days, a complete healing was obtained, together with the recovery of the normal trophism. The reparation obtained thanks to the differentiation of the stem cells in the interested district is proved by the complete lack of residual scars.

In a similar way, a male patient, aged 69, suffering from erysipela, carrying a caval filter, previously submitted to aorto-femural bilateral by-pass, who had also a preceding deep venous popliteal thrombosis in the left leg and a preceding pulmonary embolism, before the therapy showed a wide cutaneous ulcer on the left leg. The patient was treated with the gel composition of Example 3, every day, with successive application of bandaging, for a total period of twenty days. At the end of the treatment the ulcer was completely healed and the skin recovered its original aspect.

To another patient, affected by spinalioma in advanced form at the right hand, the middle finger was amputated and the little finger was seriously compromised.

Said finger, after a thirty days treatment with occlusive applications of the gel composition of Example 3 (together with brief treatments of superficial cryotherapy) recovered functionality and appearance almost completely.

Another patient, suffering from spinocellular epithelioma at the right ear, was treated, twice a day for seven days, with the gel composition of Example 3.

In this case too the complete resolution of the lesion, without residual traces of the same, was obtained. The programmed surgical operation was cancelled.

The following Examples from 1 to 4 illustrate some of the preferred mixtures of the active ingredients of the invention.

EXAMPLE 1

A gel composition containing 0.6% by weight, with reference to the total weight of the composition, of the following mixture (at 96.5%) of the phytosterols of the invention was formulated:

| | |
|---|---|
| stigmasterol (Delta 5-C22 unsaturated) | 0.0042% |
| Delta 5-avenasterol (Delta 5-C24 unsaturated) | 0.03% |
| Delta 7-avenasterol (Delta 7-C24 unsaturated) | 0.0255% |
| brassicasterol (Delta 5-C22 unsaturated) | 0.21% |
| Delta 5-C24-stigmastadienol (Delta 5-C24 diene unsaturated) | 0.19% |
| clerosterol (Delta 8-C25 unsaturated) | 0.085% |
| Delta 7-stigmastenol | 0.034% |

The percent part of the composition lacking to 100% includes a traditional mixture comprising isodecyl-laurate, isodecyl citrate, C10-C18 triglycerides, isodecyl salicylate, silica, wherein said co-formulants have a reciprocal weight ratio such as to provide a gel with high skin penetrability.

EXAMPLE 2

A cream containing 0.6% by weight of the following mixture of active principles of the invention was formulated:

| | |
|---|---|
| cholesterol | 0.36% |
| Beta-sitosterol | 0.01% |
| 24-methylene-cholesterol | 0.042% |
| Delta 5,23-stigmastadienol | 0.025% |
| campestanol | 0.034% |
| sitostanol | 0.085% |
| campesterol | 0.042% |

The percent part of the composition lacking to 100% includes a traditional mixture comprising polyisoprene, liquid paraffin, silica, wherein said co-formulants have a reciprocal weight ratio such as to provide a cream with high skin penetrability.

EXAMPLE 3

An oleogel containing 10% by weight of the following mixture of active principles of the invention was formulated:

| | |
|---|---|
| cholesterol; | 0.5% |
| brassicasterol (Delta 5-C22 unsaturated); | 3.6% |
| 24-methylene-cholesterol; | 0.3% |
| campesterol; | 24.9% |
| campestanol; | 1.1% |
| stigmasterol (Delta 5-C22 unsaturated); | 22.7% |
| Delta 5-C23-stigmastadienol; | 0.5% |
| clerosterol (Delta 8-C25 unsaturated); | 0.4% |
| Beta-sitosterol; | 43.1% |
| sitostanol; | 1.7% |
| Delta 5-avenasterol (Delta 5-C24 unsaturated); | 0.5% |
| Delta 5-C24-stigmastadienol (Delta 5-C24 diene unsaturated); | 0.3% |
| Delta 7-stigmastenol | 0.4% |

The percent part of the composition lacking to 100% is preferably formed by the co-formulants of the preceding Example 1, but can also be constituted by similar mixtures commonly used in the field for obtaining high skin penetrability.

EXAMPLE 4

A paste containing 8% by weight of the following mixture of active principles of the invention was formulated:

| | |
|---|---|
| cholesterol; | 0.5% |
| brassicasterol (Delta 5-C22 unsaturated); | 3.6% |
| 24-methylene-cholesterol; | 0.3% |
| campesterol; | 24.9% |
| campestanol; | 1.1% |
| stigmasterol (Delta 5-C22 unsaturated); | 22.7% |
| Delta 5-C23-stigmastadienol; | 0.5% |
| clerosterol (Delta 8-C25 unsaturated); | 0.4% |
| Beta-sitosterol; | 43.1% |
| sitostanol; | 1.7% |
| Delta 5-avenasterol (Delta 5-C24 unsaturated); | 0.5% |
| Delta 5-C24-stigmastadienol (Delta 5-C24 diene unsaturated); | 0.3% |
| Delta 7-stigmastenol | 0.4% |

The percent part of the composition lacking to 100% is preferably formed by the co-formulants of the preceding Example 2, but can also be constituted by similar mixtures commonly used in the field for obtaining high skin penetrability.

The invention claimed is:

1. A pharmaceutical composition comprising as active ingredient a mixture of:

| | |
|---|---|
| cholesterol | 0.5% |
| brassicasterol (Delta 5-C22 unsaturated) | 3.6% |
| 24-methylene-cholesterol | 0.3% |
| campesterol | 24.9% |
| campestanol | 1.1% |
| stigmasterol (Delta 5-C22 unsaturated) | 22.7% |
| Delta 5-C23-stigmastadienol | 0.5% |
| clerosterol (Delta 8-C25 unsaturated) | 0.4% |
| Beta-sitosterol | 43.1% |
| sitostanol | 1.7% |
| Delta 5-avenasterol (Delta 5-C24 unsaturated) | 0.5% |
| Delta 5-C24-stigmastadienol (Delta 5-C24 diene unsaturated) | 0.3% |
| Delta 7-stigmastenol | 0.4% | in combination with suitable excipients or carriers.

2. The pharmaceutical composition according to claim 1, wherein the pharmaceutical composition is administered topically, transdermally, or transmucosally.

3. The pharmaceutical composition according to claim 1, wherein the active ingredient is present at 0.001-25% by weight of the total weight of the composition.

4. The pharmaceutical composition according to claim 1, wherein the pharmaceutical composition is in the form of a gel, a cream, an oleogel, or a paste.

5. An oleogel composition comprising 10% by weight of the pharmaceutical composition of claim 1.

6. A paste comprising 8% by weight of the pharmaceutical composition of claim 1.

7. A method of inducing proliferation and differentiation of stem cells in an adult organism, comprising administering to the organism a pharmaceutical composition comprising as active ingredient a mixture of:

| | |
|---|---|
| cholesterol | 0.5% |
| brassicasterol (Delta 5-C22 unsaturated) | 3.6% |
| 24-methylene-cholesterol | 0.3% |
| campesterol | 24.9% |
| campestanol | 1.1% |
| stigmasterol (Delta 5-C22 unsaturated) | 22.7% |
| Delta 5-C23-stigmastadienol | 0.5% |
| clerosterol (Delta 8-C25 unsaturated) | 0.4% |
| Beta-sitosterol | 43.1% |
| sitostanol | 1.7% |
| Delta 5-avenasterol (Delta 5-C24 unsaturated) | 0.5% |
| Delta 5-C24-stigmastadienol (Delta 5-C24 diene unsaturated) | 0.3% |
| Delta 7-stigmastenol | 0.4% | in combination with suitable excipients or carriers.

* * * * *